United States Patent
Taniguchi

(10) Patent No.: US 11,495,358 B2
(45) Date of Patent: Nov. 8, 2022

(54) VIRTUAL REALITY VIDEO REPRODUCTION APPARATUS, AND METHOD OF USING THE SAME

(71) Applicant: Sumitomo Pharma Co., Ltd., Osaka (JP)

(72) Inventor: Masaru Taniguchi, Tokyo (JP)

(73) Assignee: Sumitomo Pharma Co., Ltd., Osaka (JP)

(*) Notice: Subject to any disclaimer, the term of this patent is extended or adjusted under 35 U.S.C. 154(b) by 0 days.

(21) Appl. No.: 17/465,285

(22) Filed: Sep. 2, 2021

(65) Prior Publication Data

US 2021/0398686 A1 Dec. 23, 2021

Related U.S. Application Data

(63) Continuation of application No. PCT/JP2020/004565, filed on Feb. 6, 2020.

(51) Int. Cl.
| | | |
|---|---|---|
| *G06T 1/00* | (2006.01) | |
| *G16H 50/50* | (2018.01) | |
| *G16H 20/70* | (2018.01) | |
| *G06F 3/16* | (2006.01) | |
| *G06T 3/00* | (2006.01) | |
| *G06T 5/00* | (2006.01) | |

(Continued)

(52) U.S. Cl.
CPC ............ *G16H 50/50* (2018.01); *G06F 3/16* (2013.01); *G06T 3/0012* (2013.01); *G06T 5/002* (2013.01); *G06T 5/20* (2013.01); *G06T 19/006* (2013.01); *G16H 20/70* (2018.01); *G06T 2207/10016* (2013.01); *G06T 2210/41* (2013.01)

(58) Field of Classification Search
CPC .......................... G06T 19/003; G06T 19/006
See application file for complete search history.

(56) References Cited

U.S. PATENT DOCUMENTS

| | | | |
|---|---|---|---|
| 2011/0055746 A1* | 3/2011 | Mantovani | B63C 11/26 715/848 |
| 2016/0364915 A1* | 12/2016 | Smith | G06T 13/80 |
| 2018/0090029 A1 | 3/2018 | Fisher et al. | |

(Continued)

FOREIGN PATENT DOCUMENTS

| | | |
|---|---|---|
| JP | 2019-537459 A | 12/2019 |
| WO | 2017/191847 A1 | 11/2017 |

OTHER PUBLICATIONS

Jin et al., Simulation of Eye Disease in Virtual Reality, Proceedings of the 2005 IEEE Engineering in Medicine and Biology 27th Annual Conference, Sep. 2005, pp. 5128-5131 (Year: 2005).*

(Continued)

*Primary Examiner* — Charles Tseng

(74) *Attorney, Agent, or Firm* — Studebaker & Brackett PC

(57) ABSTRACT

The present invention has an object to provide a virtual reality video reproduction apparatus that can allow a viewer to experience an impairment due to a disease, such as diabetes, with a strong sense of immersion. The virtual reality video reproduction apparatus of the present invention applies a filter process of simulating a visual impairment caused by diabetes to a predetermined area of images included in a virtual reality video that represents virtual reality content, and causes an electronic display included in a virtual reality headset to display the video.

14 Claims, 14 Drawing Sheets

(51) Int. Cl.
G06T 5/20 (2006.01)
G06T 19/00 (2011.01)

(56) References Cited

U.S. PATENT DOCUMENTS

2018/0254097 A1* 9/2018 Gani .................... G06T 19/003
2019/0380659 A1   12/2019 Ohkuma et al.

OTHER PUBLICATIONS

Stock et al., Realistic Simulation of Progressive Vision Diseases in Virtual Reality, VRST 2018: 24th ACM Symposium on Virtual Reality Software and Technology, Nov.-Dec. 2018 (Year: 2018).*
International Search Report issued in PCT/JP2020/004565, dated Apr. 7, 2020.
Written Opinion of the International Searching Authority issued in PCT/JP2020/004565 dated Apr. 7, 2020.
Office Action issued in JP 2020-168955; mailed by the Japanese Patent Office dated Nov. 12, 2020.
Health and beauty blog 'HAKUR'; "App that allows you to experience eye diseases using a smartphone or VR viewer to deepen your understanding of them 'ViaOpta Simulator', 'ViaOpta EyeLife'" [online] Dec. 25, 2018 <URL:https://hakuraidou.com/blog/95969/>.
Mogura VR; "Efforts by Carl Zeiss to have people experience and understand visual impairments in VR" [online] Mar. 9, 2018 <URL:https://www.moguravr.com/carl-zeiss-vr/>.
Shoichiro Fujisawa et al.; "Development of visual impairment experience system using AR technology" The 22nd Annual Conference of the Virtual Reality Society of Japan, Sep. 27, 2017, 1B3 06.

* cited by examiner

VIRTUAL REALITY VIDEO REPRODUCTION APPARATUS, AND METHOD OF USING THE SAME

TECHNICAL FIELD

The present disclosure relates to a virtual reality video reproduction apparatus, and a method of using the same, and more specifically, to a virtual reality video reproduction apparatus that provides an experience of a visual impairment caused by diabetes through virtual reality, and a method of using the same.

BACKGROUND ART

With widespread of the virtual reality (VR) technology, its application field has been increasing. Also in the medical field, the virtual reality technology has been increasingly used. For example, there is a system that simulates medical procedures in a virtual reality operating room for training a trainee, such as a doctor (Patent Literature 1). The system is for simulating medical procedures in a virtual reality operating room for training a trainee, and includes: a user input device; a medical tool; a medical procedure simulation system that receives input from the user input device and the medical tool to execute the simulation of the selected medical procedure; a virtual reality simulation system coupled to the medical procedure simulation system to render a virtual reality operating room scene that corresponds to the type of medical procedure to simulate, and the simulation of the selected medical procedure into a virtual reality scene; and a virtual reality headset coupled to the virtual reality simulation system for allowing the trainee to view the virtual reality scene. Accordingly, a medical simulator can provide a medical procedure simulation for the trainee in virtual reality. The technology provides a medical procedure simulation for a doctor trainee, and is recognized to have an advantageous effect of being capable of improving the medical skills of the trainee. It is understood that when a patient gets a medical care from the trained doctor, the patient can get a more appropriate medical care for treatment.

CITATION LIST

Patent Literature

Patent Literature 1

Japanese Translation of PCT International Application Publication No. 2019-537459

SUMMARY OF INVENTION

Technical Problem

There are diseases that require patients or potential patients to abstain for the sake of treatment or prevention. For example, diabetes requires improvement in a lifestyle habit, such as appropriate food and enforcement of exercise. However, this improvement is against instincts, such as appetite, or consumes vitality. Accordingly, the patients are required to abstain rigorously. Potential diabetes patients are also required to abstain similarly for the sake of preventing diabetes from developing. To continuously execute such self-abstention for improving a lifestyle habit, potential diabetes patients are required to be strongly-minded. For achievement thereof, it is very important to strongly motivate potential diabetes patients and the like to improve a lifestyle habit. As part of treatment and the like, advice for improving a lifestyle habit has been provided for potential diabetes patients and the like by doctors and the like. Eventually, the advantageous effects depend on how the potential diabetes patients and the like are aware of the necessity for improving a lifestyle habit. Accordingly, simply providing the advice does not necessarily succeed. If a potential diabetes patient has developed diabetes or if the symptoms of a diabetes patient has been exacerbated, and then, even if the patient acutely is made aware of the necessity of improving a lifestyle habit, the effects of treatment are typically limited at the time because diabetes is a chronic disease. Accordingly, taking preventive actions against diabetes is significantly important. As described above, as a measure against diseases, such as diabetes, requiring improvement in a lifestyle habit for treatment and prevention, it is important to strongly motivate potential patients to improve a lifestyle habit. However, conventionally, there is no technology usable for the sake of such motivating. The conventional technology described above provides trainees with a medical procedure simulation through virtual reality, but cannot be used for motivation for improving a lifestyle habit. The virtual reality technology strongly impresses viewers. However, the technology has never been used for motivation for improving a lifestyle habit for the sake of treatment and prevention of a chronic disease, such as diabetes. The augmented reality (AR) technology, which displays information on a real scene in an overlaid manner, has been spreading. However, the augmented reality technology has not been used for motivation for improving a lifestyle habit for treatment and prevention of a chronic disease, such as diabetes.

Solution to Problem

A virtual reality video reproduction apparatus according to the present invention has been achieved in view of the problems described above, and includes: a memory that stores content data including virtual reality content; a virtual reality headset that includes an electronic display for displaying a video about the content data; a content reproducer that generates a virtual reality video that represents the virtual reality content, from the content data; and a filter processor that executes a filter process of applying a predetermined image processing to a predetermined area of at least part of images of the virtual reality video generated, and causes the electronic display to display the video, wherein the filter process executes, as the predetermined image processing, a simulation of visual impairments caused by diabetes.

The virtual reality content may be content for providing experience of a symptom of a visual impairment, or content describing a lifestyle habit for preventing diabetes, preventing development thereof, or treatment therefor. That is, the virtual reality content may be patient experience content taken in accordance with a scenario for providing experience of a symptom of a visual impairment caused by diabetes, based on the virtual reality video where the simulation of the visual impairment is executed. The virtual reality content may include lifestyle habit description content taken in accordance with a scenario describing a lifestyle habit for preventing diabetes, preventing development thereof, or treatment therefor, after the patient experience content.

The present invention can also be configured to provide experience of a visual impairment through augmented reality (AR) by executing the simulation of the visual impairment, for forward video pictures representing a user's front scene taken by a camera, instead of the virtual reality content. That is, the virtual reality video reproduction apparatus according to the present invention can be configured to further include a camera that obtains forward video pictures ahead of the virtual reality headset, wherein the content data includes patient experience audio content that is audio content describing, by audio, a visual impairment caused by diabetes based on the forward video pictures where the simulation of the visual impairment is executed, the content reproducer further reproduces the audio description from the patient experience audio content, before reproduction of the virtual reality content, and the filter processor executes the simulation of the visual impairment for a predetermined area of at least part of images of the forward video pictures instead of the virtual reality video. The virtual reality content may include lifestyle habit description content taken in accordance with a scenario describing a lifestyle habit for preventing diabetes, preventing development thereof, or treatment therefor. The filter process may execute the simulation in which an effect of the simulation is enhanced to a predetermined intensity such that the visual impairment starts and gradually develops to a predetermined degree.

The filter process according to the present invention can be configured to execute simulations of various visual impairments. That is, the filter process can be configured to execute the simulation of the visual impairment of "loss", by darkening the predetermined area of at least part of the images. The filter process can also be configured to execute the simulation of the visual impairment of "blearedness", by blearing the predetermined area of at least part of the images. The filter process can also be configured to execute the simulation of the visual impairment of "blurredness", by blurring the predetermined area of at least part of the images. The filter process can also be configured to execute the simulation of the visual impairment of "distortion", by distorting the predetermined area of at least part of the images.

The present invention can be achieved as a method for preventing diabetes, preventing development thereof, or treatment therefor, using the virtual reality video reproduction apparatus. The method for preventing diabetes, preventing development thereof, or treatment therefor can execute a simulation of a visual impairment, for virtual reality content. That is, the present invention may be a method of using a virtual reality video reproduction apparatus, for preventing diabetes, preventing development thereof, or treatment therefor, the virtual reality video reproduction apparatus including: a virtual reality headset that includes an electronic display for displaying a video about virtual reality content; and a filter processor that executes a filter process of executing a simulation of visual impairments caused by diabetes for a predetermined area of at least part of images of a virtual reality video representing the virtual reality content, and causes the electronic display to display the video, wherein the method includes steps of: reproducing, accompanied by the filter process, patient experience content that is the virtual reality content taken in accordance with a scenario for providing experience of a symptom of visual impairments caused by diabetes, based on the virtual reality video where the simulation of the visual impairments is executed, and causing the electronic display to display the content. The method may further comprise reproducing lifestyle habit description content that is the virtual reality content taken in accordance with a scenario describing a lifestyle habit for preventing diabetes, preventing development thereof, or treatment therefor, after reproducing the patient experience content, and causing the electronic display to display the content. In the method, the filter process may execute the simulation in which an effect of the simulation is enhanced to a predetermined intensity such that the visual impairment starts and gradually develops to a predetermined degree.

In the method for preventing diabetes, preventing development thereof, or treatment therefor, the simulation of visual impairment can be configured to be executed for the forward video pictures representing the user's front scene. That is, the present invention is a method of using a virtual reality video reproduction apparatus, for preventing diabetes, preventing development thereof, or treatment therefor, the virtual reality video reproduction apparatus including: a virtual reality headset that includes a camera that obtains forward video pictures, and an electronic display for displaying the forward video pictures and a video about virtual reality content; and a filter processor that executes a filter process of executing a simulation of visual impairments caused by diabetes for a predetermined area of at least part of images of the forward video pictures, and causes the electronic display to display the video, wherein the method includes steps of; applying the filter process to the forward video pictures and causing the electronic display to display the pictures, while reproducing patient experience audio content that describes visual impairments caused by diabetes, based on the forward video pictures where the simulation of visual impairments is executed. The method may further comprise reproducing lifestyle habit description content that is the virtual reality content taken in accordance with a scenario describing a lifestyle habit for preventing diabetes, preventing development thereof, or treatment therefor, after reproducing the patient experience content, and causing the electronic display to display the content. In the method, the filter process may execute the simulation in which an effect of the simulation is enhanced to a predetermined intensity such that the visual impairment starts and gradually develops to a predetermined degree.

Advantageous Effects of Invention

The present invention applies the filter process of simulating the visual impairment caused by diabetes to the predetermined area of at least part of the images of the virtual reality video representing the virtual reality content, and causes the electronic display included in the virtual reality headset to display the video. Accordingly, an advantageous effect is exerted that allows a user viewing the virtual reality video to experience a visual impairment caused by diabetes with a sense of immersion, and can provide motivation for improving a lifestyle habit. According to the present invention, the virtual reality content can be patient experience content taken in accordance with the scenario for providing experience of the symptom of visual impairment caused by diabetes, based on the virtual reality video where the simulation of the visual impairment is executed. In this case, an advantageous effect is exerted that allows the user to experience the visual impairment that can be caused by a complication of diabetes in accordance with the scenario of patient experience content with a strong sense of immersion. According to the present invention, the virtual reality content may include lifestyle habit description content taken in accordance with the scenario describing a lifestyle habit for preventing diabetes, preventing development thereof, or treatment therefor, after the patient experience content. In this case, the user can be provided with strong motivation that is for improving a lifestyle habit required for treatment and prevention. According to the present invention, the filter process may execute the simulation in which an effect of the simulation is enhanced to a predetermined intensity such that the visual impairment starts and gradually develops to a predetermined degree. In this case, unnaturalness due to abrupt occurrence of the visual impairment after start of reproduction of the content can be resolved, and the user can be strongly impressed by seriousness of development of the symptom after start of the visual impairment.

The present invention can apply the filter process of simulating the visual impairment caused by diabetes to the predetermined area of at least part of the images of the forward video pictures taken by the camera of the virtual reality headset that obtains the forward video pictures, and cause the electronic display included in the virtual reality headset to display the pictures. In this case, an advantageous effect is exerted that can provide the user viewing the forward video pictures with experience of the visual impairment caused by diabetes with a strong sense of immersion as their own experience through augmented reality.

The present invention can also be configured to execute a simulation of a visual impairment caused by diabetes, for the virtual reality video that represents virtual reality content, for the sake of preventing diabetes, preventing development thereof, or treatment therefor, while reproducing patient experience content for providing experience of a symptom of the visual impairment caused by diabetes, and subsequently reproduce lifestyle habit description content describing a lifestyle habit for preventing diabetes, preventing development thereof, or treatment therefor. In this case, an advantageous effect is exerted that allows the user to experience the visual impairment caused by diabetes with a sense of immersion, and can provide strong motivation that is for improving a lifestyle habit required for treatment and prevention.

The present invention can also be configured to execute a simulation of a visual impairment caused by diabetes, for the forward video pictures taken by the camera, for the sake of preventing diabetes, preventing development thereof, or treatment therefor, while reproducing patient experience audio content describing a symptom of the visual impairment caused by diabetes, and subsequently reproduce lifestyle habit description content describing a lifestyle habit for preventing diabetes, preventing development thereof, or treatment therefor through virtual reality. In this case, an advantageous effect is exerted that can provide the user with experience of the visual impairment caused by diabetes with a strong sense of immersion through augmented reality, and provide strong motivation that is for improving a lifestyle habit required for treatment and prevention through virtual reality.

DESCRIPTION OF EMBODIMENTS

Two Embodiments

Typically, the present invention is implemented in two embodiments. A first embodiment is a content-based one that preliminarily creates three-dimensional virtual reality content taken from a viewpoint of a protagonist in accordance with a scenario for providing experience of a symptom of a visual impairment caused by diabetes, such as diabetic retinopathy, and executes a filter process of simulating the visual impairment during reproduction of the content, thereby allowing a user viewing the content from the viewpoint of the protagonist to experience the visual impairment. A second embodiment is based on forward video pictures, and causes a symptom of a visual impairment caused by diabetes, such as diabetic retinopathy, in an actual visual field of a user, obtains forward video pictures that represents a front scene to be in the visual field of the user at a position where the user currently resides, and applies a filter process of simulating a visual impairment to the forward video pictures, thereby providing experience of the visual impairment in real time through augmented reality. Note that part of or the entire these embodiments may be combined and executed. In this Description, the term "viewing" means that the user "views" at least a video or an image, and the user's "listening" to audio or the like is not necessarily required.

Configuration of First Embodiment (Content-Based Virtual Reality Video Reproduction Apparatus)

Figure 3:
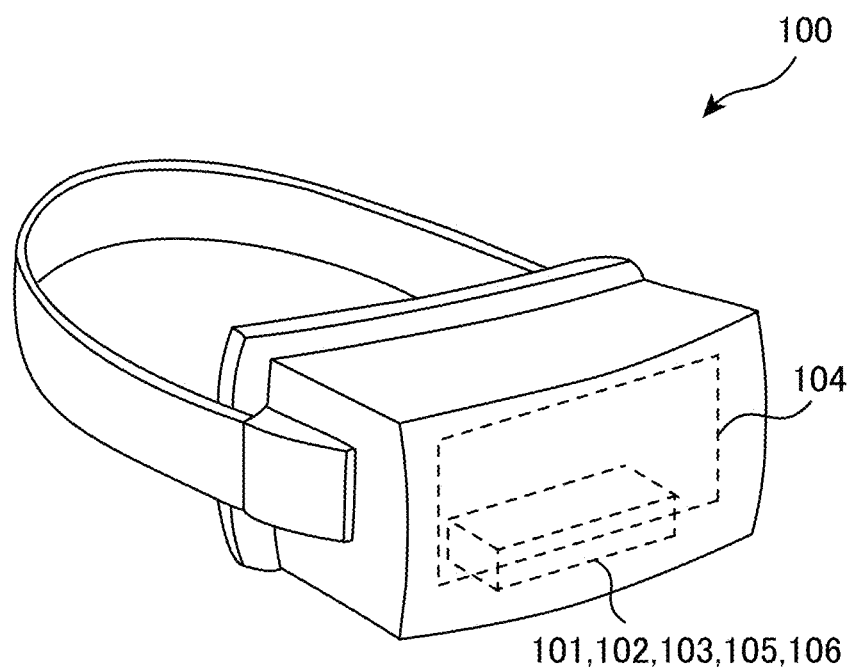
FIG. 3 shows a schematic appearance of the virtual reality video reproduction apparatus 100 according to the first embodiment of the present invention.

Hereinafter, referring to the drawings, a virtual reality video reproduction apparatus 100 according to the first embodiment of the present invention is described. FIG. 3 shows a schematic appearance of the virtual reality video reproduction apparatus 100. In FIG. 3, components represented by broken lines are components that reside in the main body of the virtual reality video reproduction apparatus 100, and cannot be viewed from the outside. FIG. 3 shows components indicated by reference numerals 101 to 106. The details of these components are described later with reference to FIG. 1. The virtual reality video reproduction apparatus 100 is an apparatus that allows the user to view content for providing experience of a symptom of a visual impairment caused by diabetes, such as diabetic retinopathy, and subsequently allows the user to view content describing a lifestyle habit for preventing diabetes, preventing development thereof, or treatment therefor. Typically, the virtual reality video reproduction apparatus 100 is a mode of a virtual reality headset that is a head mount display (goggle) provided with an electronic display that displays a video representing three-dimensional virtual reality. Typically, an attachment band, such as a rubber band, is attached to the virtual reality video reproduction apparatus 100. The user attaches the virtual reality video reproduction apparatus 100 so as to encircle and cover the eyes, and winds the rubber band around the head, thereby attaching the virtual reality video reproduction apparatus 100 around the eyes.

Figure 1:
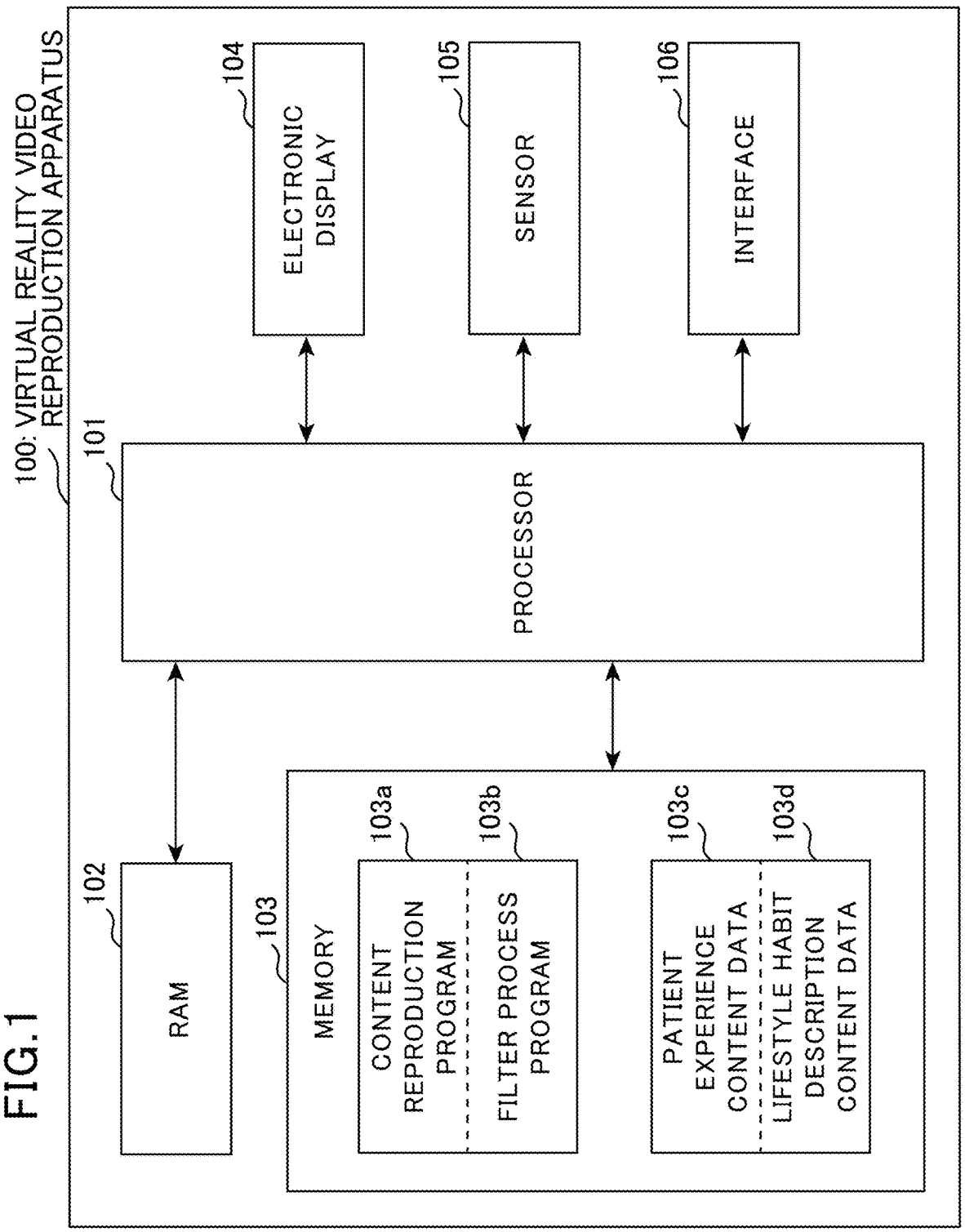
FIG. 1 is a block diagram showing the configuration of a virtual reality video reproduction apparatus 100 according to a first embodiment of the present invention.

FIG. 1 is a block diagram showing the configuration of the virtual reality video reproduction apparatus 100. The virtual reality video reproduction apparatus 100 includes a processor 101, a RAM 102, a memory 103, an electronic display 104, a sensor 105, and an interface 106. The processor 101 is a processing circuit for executing various functions of controlling operations of the virtual reality video reproduction apparatus 100, and typically, is a CPU that operates an information apparatus, such as a computer. The RAM 102 is a temporary memory, and is used as a work area while the processor 101 operates. Typically, the memory 103 is a nonvolatile memory, such as a flash ROM, and stores computer programs, and content data. The memory 103 stores a content reproduction program 103a and a filter process program 103b, as the computer programs. Typically, an OS (operating system) is used when the computer program is executed. Functions by the OS are assumed to be included in functions by the processor 101 executing the computer program. The description thereof is herein omitted. The characteristic functions of the virtual reality video reproduction apparatus 100 according to the present invention are achieved by these computer programs being executed by the processor 101 to form execution modules in accordance with such functions. The processor 101 reads the content reproduction program 103a stored in the memory 103, and executes the program using the work area of the RAM 102, thereby executing operations that achieve various functions about content reproduction. As described above, a module is formed that functions as a content reproducer that generates a virtual reality video representing virtual reality content in view in a direction toward the front of the virtual reality video reproduction apparatus 100 (three-dimensional bearing). The processor 101 reads the filter process program 103b stored in the memory 103, and executes the program using the work area of the RAM 102, thereby executing a simulation of a visual impairment, for a screen included in the virtual reality video. As described above, a module is formed that functions as a filter processor that provides a function of displaying on the electronic display 104, by executing a filter process of simulating a predetermined visual impairment in a predetermined area of images included in the generated virtual reality video. Note that the term "filter" in the filter process is what conceptually represents an overall operation of intervening in original image data and applying predetermined image processing onto part of the data, with respect to a process that is for typical image displaying and transfers the images data to the electronic display 104 to be displayed. Accordingly, the term does not further limit this "image processing". That is, the term "filter process" can be replaced with a term "process" when the image processing is specifically identified.

The memory 103 stores, as content data, patient experience content data 103c and lifestyle habit description content data 103d. The patient experience content data 103c is content data on a patient experience video in accordance with a scenario for providing experience of a visual impairment caused by diabetes. The lifestyle habit description content data 103d is content data on a lifestyle habit description video that includes a description for improving a lifestyle habit to prevent diabetes and its worsening. The patient experience content data 103c and the lifestyle habit description content data 103d are virtual reality content data represented by video data on a 360-degree video obtained by imaging an object using an omnidirectional camera or the like from the viewpoint of a protagonist of the scenario of the content in order to allow images in all the directions around the user to be reproduced. Here, the patient experience content data 103c is data characterized by including at least imageable information that can provide the user with a sense as if the user were experiencing a symptom of a visual impairment when a simulation of the visual impairment caused by diabetes is performed for a virtual reality video generated from the content data to allow the user to view the video. The lifestyle habit description content data 103d is data characterized by including at least imageable information provided for the user to improve a lifestyle habit to prevent diabetes and its worsening when the user is allowed to view a virtual reality video generated from the content data. When the content is reproduced, the lifestyle habit description content data 103d is reproduced subsequent to the patient experience content data 103c. The patient experience content data 103c and the lifestyle habit description content data 103d may be integrated data. Preferably, the patient experience content data 103c and the lifestyle habit description content data 103d include audio data to be reproduced in synchronization with the video. The patient experience content data 103c may include scenario data for controlling the operation of the virtual reality video reproduction apparatus 100, for instance, for activating and stopping a predetermined process, such as a filter process of images at predetermined timing in synchronization with the video, when the content data is reproduced. Accordingly, the scenario of the content allows a process of starting image processing of the simulation of visual impairment, for the virtual reality video, at timing when the visual impairment of the protagonist starts in their field.

The electronic display 104 is a flat panel display, such as an LCD (liquid crystal display) or an organic EL display, and displays images of a video about content data that includes virtual reality content, for the user wearing the virtual reality video reproduction apparatus 100 around the eyes, through eyepieces arranged on the user side. When the data of the images to be displayed is transferred to a data buffer area of the electronic display 104, the electronic display 104 reads the data of the images from the data buffer area, and displays the images represented by the data. Although not shown, the virtual reality video reproduction apparatus 100 further includes a speaker for outputting audio in synchronization with the video, and a circuit that drives the speaker.

The sensor 105 is a sensor for detecting the direction toward the front of the virtual reality video reproduction apparatus 100, that is, the direction of the line of sight of the user. The sensor 105 is a sensor that detects the movement, position and direction, such as a gyroscope sensor, an acceleration sensor and a direction sensor. The interface 106 is a user interface through which information, such as on an operation instruction, is input from the user, and information representing the operation state is output to the user, and includes, operation buttons, a remote controller interface, LEDs, and a circuit that drives these components.

Content Data

The patient experience video of the patient experience content data 103c includes virtual reality content for allowing the user to experience a symptom of a visual impairment caused by diabetes on the basis of the virtual reality video where the simulation of visual impairment is executed. This is a virtual reality video taken from the viewpoint of the protagonist of the scenario of the content, and is, for example, a 360-degree video allowing the user to view an object, such as the inside of a certain room, from the viewpoint of the protagonist sitting in the room, in any direction. Here, a result of image processing that represents the symptom of the visual impairment is not included in the original video itself. If the result of image processing representing the symptom of the visual impairment including, for example, "loss" of the visual field were included in the original video, the position of the visual impairment would be fixed at a specific position of the object, such as the room. In this case, if the user moved the line of sight, the position of the visual impairment to be moved accordingly would not be moved. Accordingly, the user could not have a sense of immersion as if the user themself had the visual impairment. In order to simulate the visual impairment, the simulation of a predetermined visual impairment is executed for a predetermined area of images included in the virtual reality video to be displayed on the electronic display, through the filter process, during reproduction of the video. The execution result is overlaid on the images. As described above, the patient experience video of the patient experience content data 103c is for allowing the user to experience the symptom of the visual impairment on the basis of the virtual reality video where the simulation of visual impairment is executed, and has been taken in accordance with a scenario therefor. The video is the virtual reality video. Accordingly, when the user looks in any direction around themself, they can view images, such as of the inside of a room corresponding to the direction. Execution of a filter process of simulating the visual impairment during reproduction thereof allows the user to view the inside of the room in a state of having the visual impairment. As described above, during reproduction of the patient experience video, a result of image processing of simulating the visual impairment appears in a manner of being overlaid on a predetermined position of the user's visual field. Accordingly, the user can obtain a sense of immersion as if they had the visual impairment. The user can thus experience the state of having the visual impairment with a sense of reality. Preferably, the degree of the simulated visual impairment does not represent a state where the visual impairment develops immediately after start of reproduction of the content, but is such that the visual impairment starts in a predetermined period during reproduction and gradually develops to a predetermined degree. That is, preferably, the filter process includes a process of enhancing the effect of the simulation of visual impairment in a predetermined period during which the virtual reality video is displayed. According to such a configuration, unnaturalness due to abrupt occurrence of the visual impairment after start of reproduction of the content can be resolved, and the user can be strongly impressed by seriousness of development of the symptom after start of the visual impairment. As a specific scenario, a story is conceivable that the visual impairment starts when a patient as a protagonist views the television, the impairment gradually develops and comes into the state of a considerable degree of the visual impairment, and the protagonist becomes aware of the visual impairment and embarrassed.

The patient experience content data 103c may additionally include virtual reality content that provides experience of impairments due to other typical complications of diabetes, such as dialysis treatment for diabetic nephropathy, and leg amputation due to a gangrenous leg caused by neurological damage. The scenario of dialysis treatment for diabetic nephropathy can provide, for example, a virtual reality video from the viewpoint of the protagonist siting on a chair, and use content representing a state where when they look in the direction of their arm, an dialysis device is attached to the arm. Note that in this case, the filter process for the images is not necessarily required. The scenario of leg amputation due to a gangrenous leg caused by neurological damage can provide, for example, a virtual reality video from the viewpoint of the protagonist sitting on a bed, and use content representing a state where when they look in the direction of their leg, the leg is lost by amputation. Note that also in this case, the filter process for the images is not necessarily required. Such additional content can further strongly impress the user with seriousness of complications of diabetes with a sense of immersion.

The lifestyle habit description video of the lifestyle habit description content data 103d is a video that provides advice for lifestyle habit improvement for the sake of preventing diabetes, preventing development thereof, or treatment therefor, preventing development thereof, treatment and the like. This is also a virtual reality video taken from the viewpoint of the protagonist of the scenario of the content, and is a 360-degree video allowing the user to view an object in any direction from the viewpoint of the protagonist. Through the lifestyle habit description video, for example, advice is provided that includes eating calorie-controlled food, restricting between-meal eating, appropriate exercise, and taking drugs as prescribed. A scenario may be of a mode where a conversation about lifestyle habit improvement is started with the protagonist as the person of the viewpoint, and the protagonist replies thereto. As a specific scenario, a style is conceivable where the protagonist sees a doctor in their office, and the doctor gives advice to the protagonist. A scenario or the like is also conceivable where the protagonist takes advice on food and medication during eating with their family at home, and takes advice by their family on exercise, for example, how about exercising together. As described above, the lifestyle habit description video of the lifestyle habit description content data 103d is for describing a lifestyle habit for preventing diabetes, preventing development thereof, or treatment therefor, and has been taken in accordance with a scenario therefor. The lifestyle habit description video is thus provided through virtual reality, which allows the user to take appropriate advice for preventing diabetes, preventing development thereof, or treatment therefor as if they were advised on site with a sense of immersion.

Visual Impairment Filter Process

As filter processes of simulating visual impairments, for example, processes of executing types of simulation of "loss", "blearedness", "blurredness", "distortion" and the like may be used. FIGS. 7 to 10 show change in visual field due to various visual impairments through deformation of a lattice pattern. In the filter process, through reproduction of the patient experience content data 103c, image processing is executed for data on each image deployed on the RAM 102 or the like in every screen refresh cycle, by the processor 101 manipulating pixel data, thereby executing image processing to deform the original image.

Figure 7:
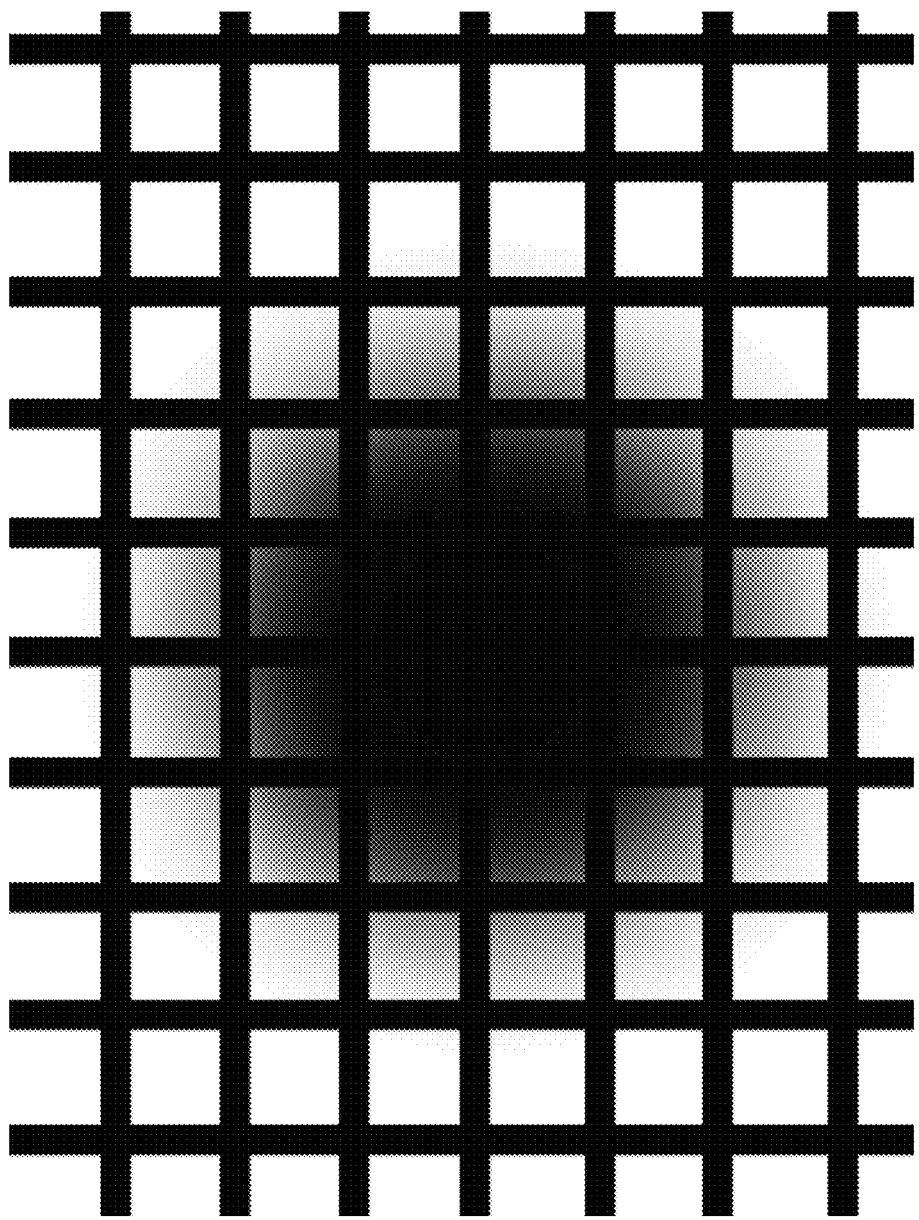
FIG. 7 shows advantageous effects of a filter process for simulating a visual impairment of "loss".

The filter process of a simulation of visual impairment of "loss" is to generate a "loss" effect of darkening a predetermined area including, for example, the center and therearound of images included in the virtual reality video. FIG. 7 shows a state where the filter process of simulating the visual impairment of "loss" has been applied to a lattice pattern image. The simulation of visual impairment of "loss" generates a dark "loss" area having a shape of a circle or the like at the part where the visual impartment is assumed to occur, such as around the center or the like, for example, of the images included in the virtual reality video. Specifically, for example, the process of "loss" provides, on the RAM 102, a memory area (layer) for another image having the same screen resolution as the image to be image-processed, and arranges pixels having low values (luminances), such as of black or dark gray, in a predetermined area to which the "loss" process is to be applied on the layer, while arranging white pixels in the other areas, to thereby prepare a layer for the "loss" process, and executes computation, such as multiplication and comparative dark composition, for pixels of the image to be image-processed, with the respective pixels on the layer for the "loss" process at the same positions, thereby reducing the luminances. The degree of reduction in luminance, which is the degree of the effect of the simulation, can be defined by the lower degree of luminances of the pixels on the layer for the "loss" process. Note that it is preferable to perform a process where reduction in values of pixels around the center of the "loss" area on the layer for the "loss" process significantly reduces the luminances of pixels around the center of the "loss" area of the image to be image-processed to achieve further darkening, and gradual reduction in degree of reduction of luminances with approaching the periphery of the "loss" area obscures the boundary. Accordingly, the visual impairment of "loss" where the center and the like of the visual field is dark and the object is difficult to view is simulated.

Preferably, a predetermined period during content reproduction includes a period where the visual impairment occurs and the degree thereof gradually develops. To achieve this, the filter process performs a process that does not perform the image processing at all at the beginning, starts the simulation of visual impairment in a predetermined period during displaying of the virtual reality video, and increases the effect up to a predetermined intensity. Here, increase in the effect of the simulation of visual impairment can be achieved by enlarging the area of the visual impairment, increasing the amount of application of deformation representing the visual impairment, or combination thereof. The process of causing and increasing the effect of the simulation of visual impairment as described above is also applicable to the other types of visual impairments. The number of types of visual impairments to be simulated during content reproduction is not limited to one. Alternatively, multiple types of visual impairments may be sequentially simulated. Further alternatively, visual impairments where multiple types of visual impairments are combined may be simulated.

Figure 8:
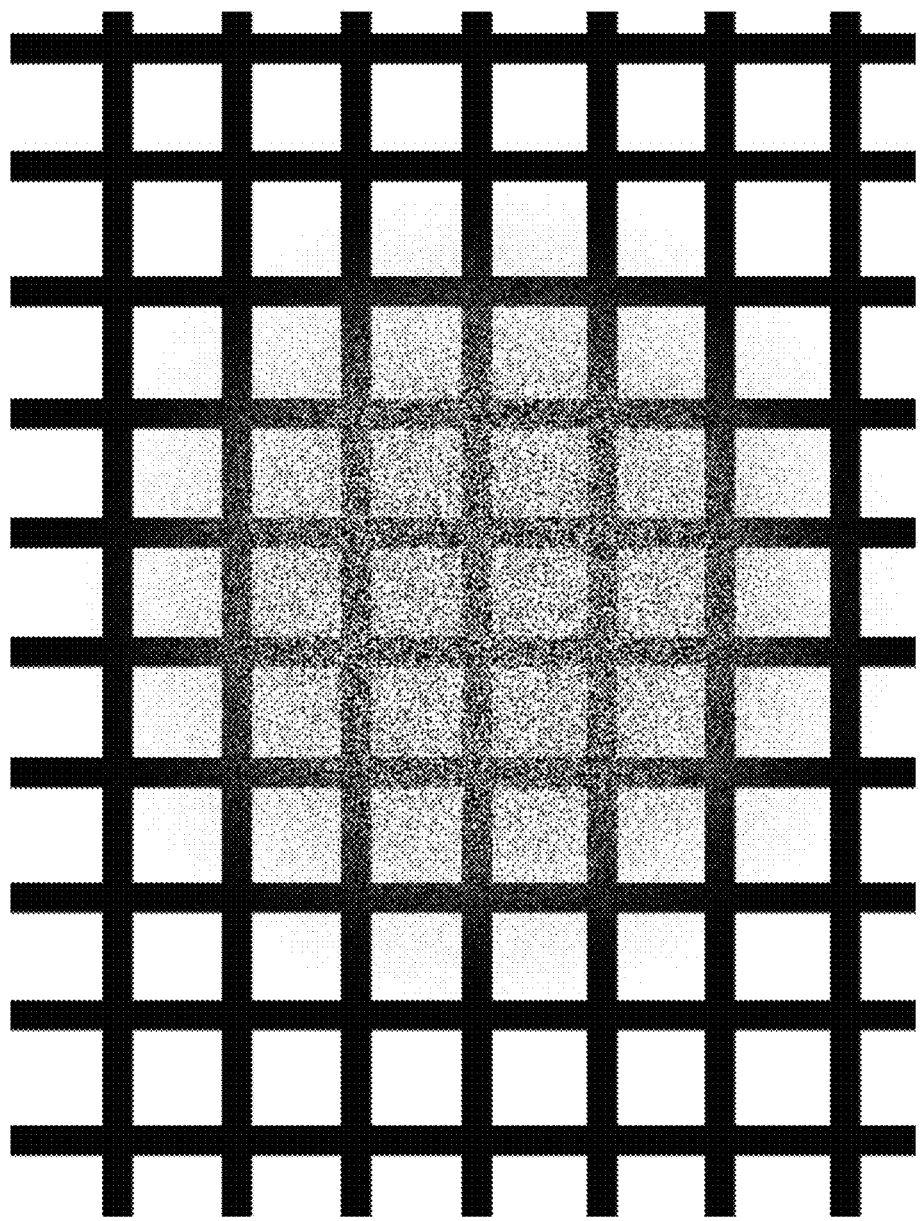
FIG. 8 shows advantageous effects of a filter process for simulating a visual impairment of "blearedness".

The filter process of a simulation of visual impairment of "blearedness" is to generate a "blearedness" effect of blearing a predetermined area including, for example, the center and therearound of images included in the virtual reality video. FIG. 8 shows a state where the filter process of simulating the visual impairment of "blearedness" has been applied to a lattice pattern image. The filter process of the simulation of visual impairment of "blearedness" adds random noise to pixels in a predetermined area including the center and therearound of images included in the virtual reality video. Specifically, the process of "blearedness" can be executed by replacing pixels at random positions in the predetermined area to be processed, with pixels having relatively high luminances, such as of white or light gray, for example. The process of "blearedness" may be executed by providing, on the RAM 102, a memory area (layer) for another image having the same screen resolution as the image to be image-processed, and arranges, as noise, white or light gray pixels at random positions in a predetermined area to which the "blearedness" process is to be applied to thereby prepare a layer for the "blearedness" process, and executing computation, such as comparative bright composition, for pixels of the image to be image-processed, with the respective pixels on the layer for the "blearedness" process at the same positions. The degree of intensity of "blearedness", which is the degree of the effect of the simulation, can be defined by the intensities of pixels to be added as noise, the luminances of noise pixels and the like. The pixels to be added as noise may be those having a predetermined value (luminance) or those having values varying in a certain range. Note that to suppress the granularity of noise, an obscuring process with a relatively small application range (about several pixels) may be performed after application of noise. The simulation of visual impairment of "blearedness" generates a "blearedness" area having a shape of a circle or the like at the part where the visual impartment is assumed to occur, such as around the center or the like, for example, of the image of the virtual reality video. The process of obscuring the boundaries is then performed by increasing the density of noise to be added to the center and therearound of the "blearedness" area to thereby apply strong blearedness to the center and therearound, and by reducing the density of noise as going outward in the "blearedness" area. Accordingly, the visual impairment of "blearedness" where the center and the like of the visual field is bleared and the object is difficult to view is simulated.

Figure 9:
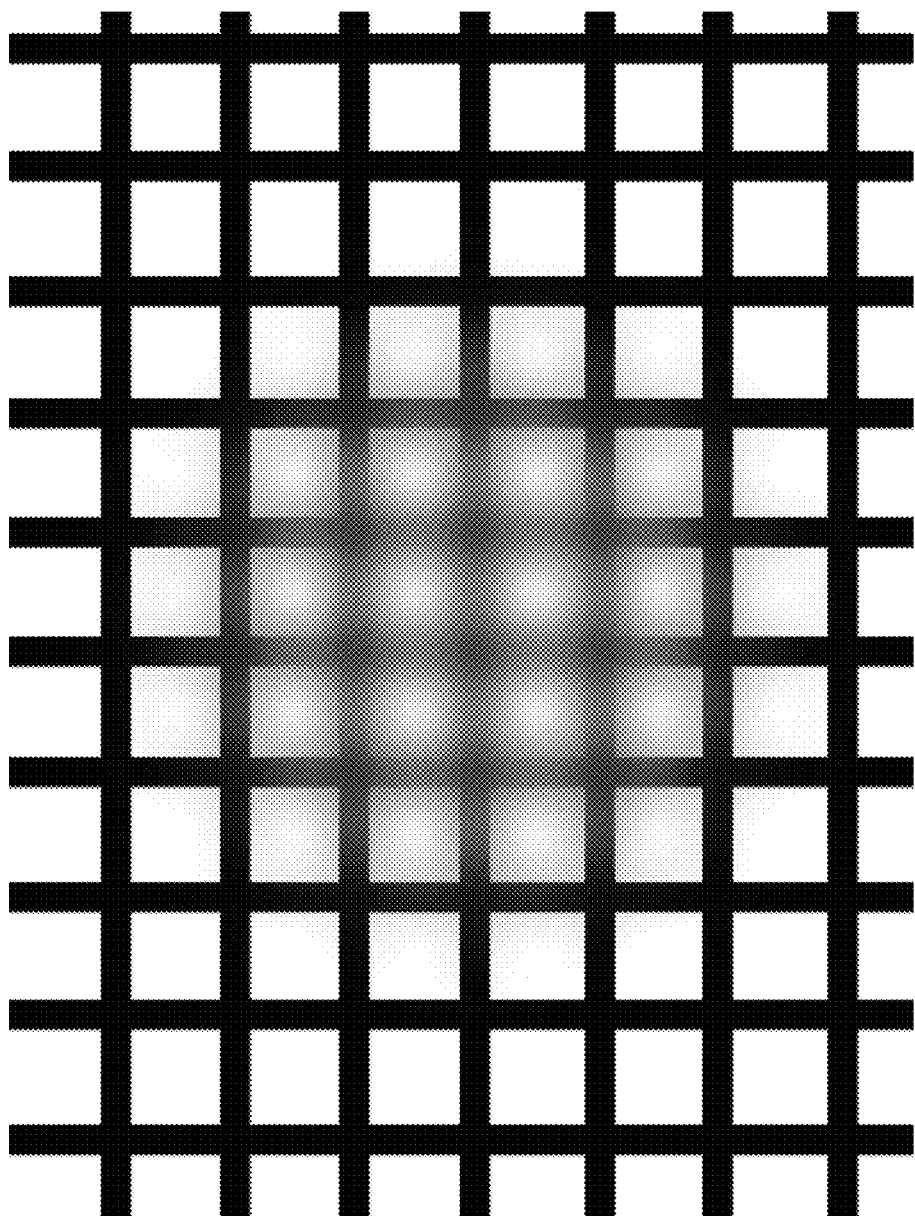
FIG. 9 shows advantageous effects of a filter process for simulating a visual impairment of "blurredness".

The filter process of a simulation of visual impairment of "blurredness" is to generate a "blurredness" effect of blurring a predetermined area including the center and therearound of images included in the virtual reality video. FIG. 9 shows a state where the filter process of simulating the visual impairment of "blurredness" has been applied to a lattice pattern image. The filter process of the simulation of visual impairment of "blurredness" executes the "obscuring" process, such as of Gaussian obscuring, for the pixels in the predetermined area including, for example, the center and therearound of the image included in the virtual reality video. Specifically, the Gaussian obscuring process can be executed by smoothing the individual pixels in the predetermined area to be processed, with weighting decreasing with increase in distance based on a Gaussian distribution for multiple pixels close to the pixels concerned in the application range of the process (replacement with average values of what are obtained by multiplying close pixels in the process application range and weights thereof). The degree of intensity of "blurredness", which is the degree of the effect of the simulation, can be defined by the application range of the obscuring process and the like. The simulation of visual impairment of "blurredness" generates a "blurredness" area having a shape of a circle or the like at the part where the visual impairment is assumed to occur, such as around the center or the like, for example, of the image of the virtual reality video. The process of obscuring the boundaries is performed by performing the strong obscuring process at the center and therearound of the "blurredness" area to achieve obscuring, and by reducing the degree of the obscuring process as going outward in the "blurredness" area. Accordingly, the visual impairment of "blurredness" where the center and the like of the visual field are blurred and the object is difficult to view is simulated.

Figure 10:
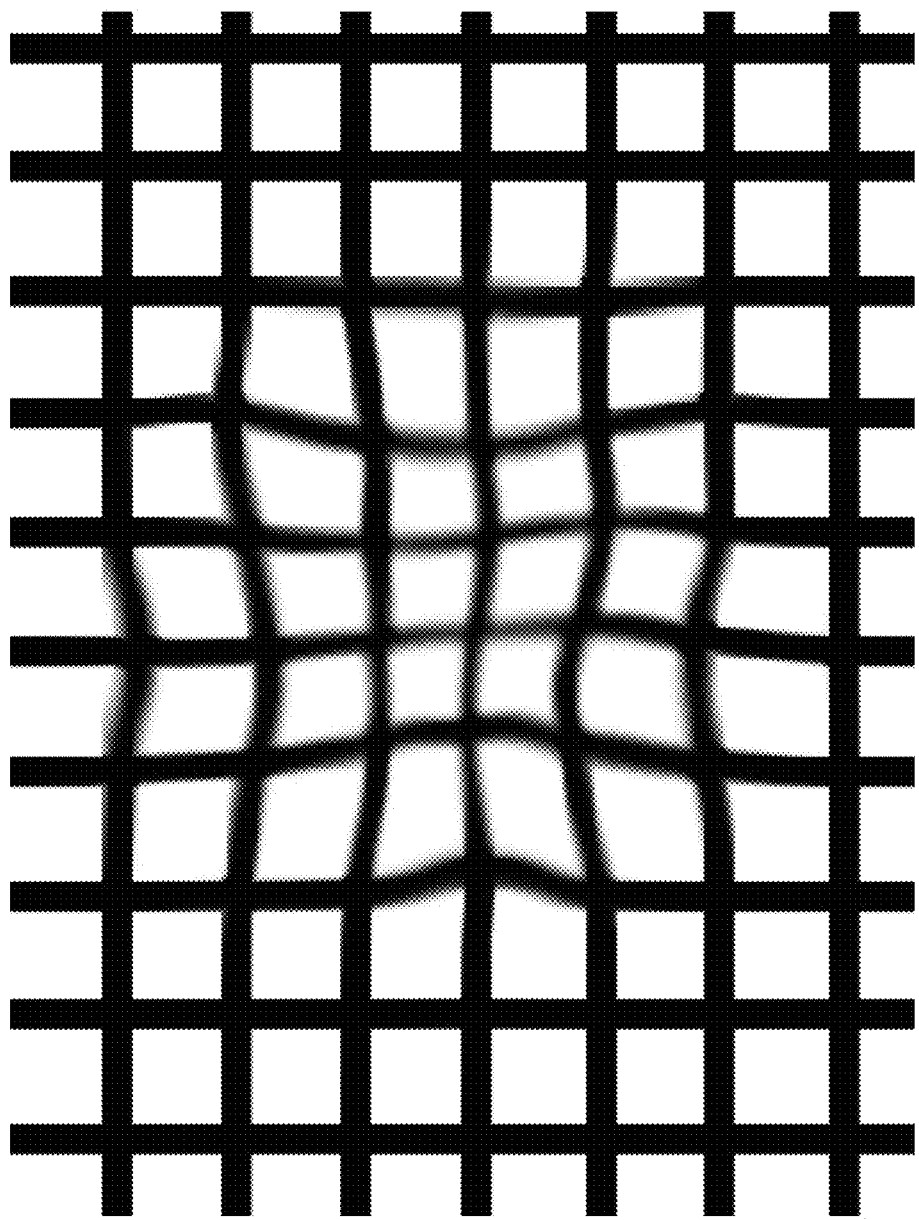
FIG. 10 shows advantageous effects of a filter process for simulating a visual impairment of "distortion".

The filter process of a simulation of visual impairment of "distortion" is to generate a "distortion" effect of distorting a predetermined area including, for example, the center and therearound of images included in the virtual reality video. FIG. 10 shows a state where the filter process of simulating the visual impairment of "distortion" has been applied to a lattice pattern image. The filter process of simulating the visual impartment of "distortion" executes a distortion process of moving the pixels in a predetermined area including, for example, the center and therearound of the virtual reality video in random directions by random amounts of movement. Specifically, the "distortion" process can be executed by a process and the like of moving the individual pixels in the predetermined area to be processed in random moving directions by random amounts of movement so as not to be largely different in moving directions and amounts of movement from close pixels (details of the original image remain at least partially); moving is replacement of values of the pixels at movement destinations with values of the pixels to be moved. The degree of intensity of "distortion", which is the degree of the effect of the simulation can be defined by the amounts of movement of pixels and by randomness of the moving directions. The simulation of visual impairment of "distortion" generates a "distortion" area having a shape of a circle or the like at the part where the visual impairment is assumed to occur, such as around the center or the like, for example, of the virtual reality video. The process of obscuring the boundaries is performed by largely distorting the center and therearound of the "distortion" area through increase in amounts of movement of pixels, while reducing the amounts of movement of pixels to reduce the degree of distortion process as going outward in the "distortion" area. Accordingly, the visual impairment of "distortion" where the center and the like of the visual field is distorted and the object is difficult to view is simulated.

Operation of First Embodiment (Content-Based Virtual Reality Video Reproduction Apparatus)

Figure 5:
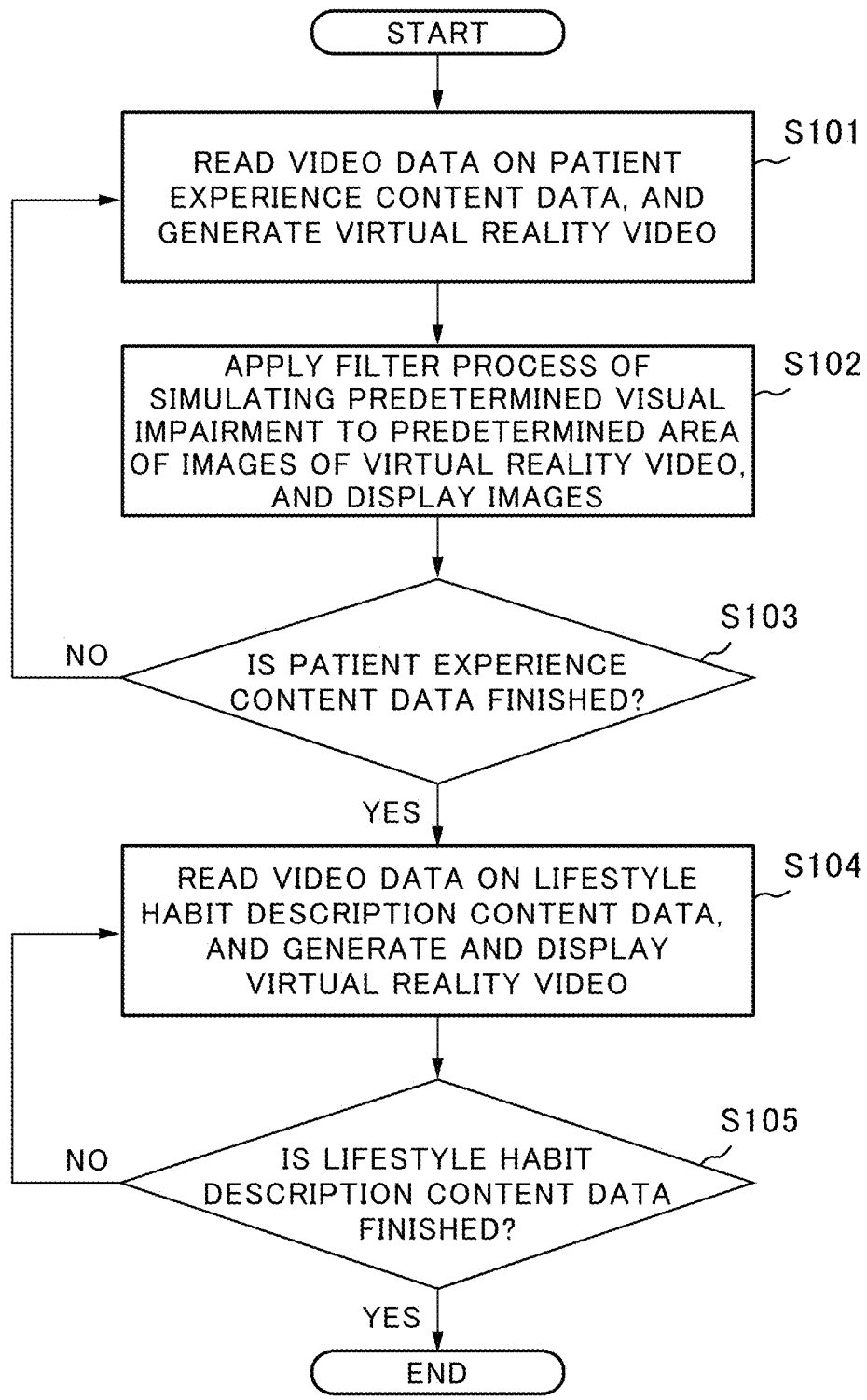
FIG. 5 is an operation flow diagram of the virtual reality video reproduction apparatus 100 according to the first embodiment of the present invention.

Next, the operation of the virtual reality video reproduction apparatus 100 is described. FIG. 5 is an operation flow diagram of the virtual reality video reproduction apparatus 100 according to the first embodiment. When an instruction for content reproduction is input, the virtual reality video reproduction apparatus 100 first reads video data on the patient experience content data 103c and generates the virtual reality video, through the operation of the content reproducer formed by execution of the content reproduction program 103a (step S101). That is, the virtual reality video reproduction apparatus 100 sequentially reads, from the memory 103, a series of images of the 360-degree video of the patient experience video of the patient experience content data 103c, decodes the images if they are encoded video data, takes data on the images constituting the video, and deploys the data on the RAM 102. The virtual reality video reproduction apparatus 100 takes, from the data on decoded images, an area of the images to be viewed in the direction toward the front of the virtual reality video reproduction apparatus 100 detected by the sensor 105 (direction of the user's line of sight), thereby generating the images constituting the virtual reality video that provides the user with a view as if the user viewing the video felt on site in a three-dimensional space. At this time, if necessary, the coordinates of individual pixels are transformed in order to transform the images constituting the 360-degree video on the basis of appropriate perspective centered on the position of the direction of the line of sight of the virtual reality video reproduction apparatus 100, so as to achieve images with a natural sense of perspective when the electronic display 104 is viewed through the eyepieces. As described above, the virtual reality video is generated by generating, one after another, images obtained by capturing an area to be displayed on the electronic display 104 from images obtained by transforming the images constituting the 360-degree video of the patient experience content data 103c on the basis of appropriate perspective centered on a position in the line of sight of the virtual reality video reproduction apparatus 100.

Figure 11:
FIG. 11 shows an example of a screen of content where the visual impairment of "loss" is overlaid.

Next, the virtual reality video reproduction apparatus 100 applies the filter process to the virtual reality video through the operation of the filter processor formed by execution of the filter process program 103b, and causes the electronic display 104 to display the video (step S102). That is, the virtual reality video reproduction apparatus 100 applies the filter process of applying the visual impairment of "loss", "blearedness", "blurredness" or "distortion" to each of the images constituting the virtual reality video generated and deployed on the RAM 102 in step S101, thereby generating the virtual reality video where the symptom of the visual impairment is overlaid. Typically, the number of types of visual impairments to be simulated is, for example, one, which is of "loss". Alternatively, multiple types of visual impairments may be sequentially simulated. Further alternatively, visual impairments where multiple types of visual impairments are combined may be simulated. That is, the symptoms of types of visual impairments may be simultaneously simulated in the same area or a different area of the image (including a case where areas overlap with each other). As described above, the filter process is applied to the pixels constituting the area of the images where the visual impairment is to be caused such that for "loss" the values (luminances) of pixels are reduced, for "blearedness" noise of pixels at random positions are added, for "blurredness" the Gaussian obscuring process is applied to the pixels, and for "distortion" the pixels are moved in random moving directions by random amounts of movement. The filter process is applied to the predetermined area of the image of the virtual reality video. The predetermined area of the image may be a circular area including the center and therearound of the image, for example. In this case, a state is simulated where a circular area of the visual impairment is at the center of the visual field. The predetermined area may deviate from the center. In this case, a state is simulated where the visual impairment is in an area deviating from the center of the visual field. The filter-processed data on the images of the virtual reality video is transferred to the data buffer area of the electronic display 104, and the electronic display 104 reads and displays the data every refresh cycle. The user views the virtual reality video displayed on the electronic display 104 through the eyepieces, thereby viewing the object imaged in the virtual reality content as if the user viewed the object in their line of sight. Accordingly, the user gets an impression as if the object were in front. FIG. 11 shows an example of a content image where the visual impairment of "loss" is caused by the filter process at the center of the visual field of the protagonist talking with the family.

Preferably, the virtual reality video reproduction apparatus 100 increases the effect of the simulation of visual impairment in the filter process through the operation of the filter processor formed by execution of the filter process program 103b. The filter processor does not start the simulation of the visual impairment until predetermined timing during reproduction of the patient experience video of the patient experience content data 103c, and causes the visual impairment through the simulation at timing when the protagonist starts to be aware of the visual impairment along the scenario of the patient experience video, and gradually increases the effect to a predetermined intensity. Accordingly, the visual impairment can be caused at appropriate timing in the scenario. The user can be impressed with a process of developing their visual impairment, thus being strongly impressed.

The effect of the simulation of visual impairment can be increased by enhancing the area of the visual impairment, by increasing the amount of application of deformation representing the visual impairment for the image (for "loss" the degree of reducing the values (luminances) of pixels, for "blearedness" the intensity of noise of pixels at the random positions to be added to the pixels and the luminances of the noise pixels, for "blurredness" the application range of Gaussian obscuring, and for "distortion" the amount of movement of pixels), or by combination thereof. When the area of the visual impairment is enlarged, the enlarged area may have an irregular shape in order to provide a stronger impression. This also corresponds to increase in the effect of simulation of visual impairment. The scenario data that includes the start timing of the simulation of visual impairment, the period during which the effect of the simulation of visual impairment is increased, and the method of increasing the effect of the simulation of visual impairment may be included in the patient experience content data 103c, or held as other data different from the patient experience content data 103c.

Figure 12:
FIG. 12 shows an example of a screen of content representing "dialysis treatment for diabetic nephropathy".
Figure 13:
FIG. 13 shows an example of a screen of content representing "leg amputation due to a gangrenous leg caused by neurological damage".

The patient experience content data 103c may include not only the visual impairment but also content representing dialysis treatment for diabetic nephropathy as shown in FIG. 12, and content representing leg amputation due to a gangrenous leg caused by neurological damage as shown in FIG. 13. No filter process is applied to these images. However, during content reproduction, the content representing a leg or an arm having such a symptom can be seen in the case of viewing in the direction of their own leg or arm. Accordingly, an effect is exerted that provides an impression that the complications of diabetes range widely and are serious.

The virtual reality video reproduction apparatus 100 always monitors whether the reproduction of video data on the patient experience content data 103c is finished or not through the operation of the content reproducer formed by execution of the content reproduction program 103a. If not finished, the processing in the flow is returned to step S101, and the filter-processed virtual reality video of the patient experience content data 103c is continuously displayed. If finished, the processing in the flow proceeds to the next step S104 (step S103). Data identifying the time of finish of the patient experience content data 103c may be included in the patient experience content data 103c, or held as other data different therefrom. The user views the patient experience video where the visual impairment is simulated through reproduction of the patient experience content data 103c, and can experience the symptom of visual impairment caused by diabetes with a sense of immersion. Note that step S104 and thereafter indicate reproduction of the lifestyle habit description content data 103d. If only experience of the symptom of the visual impairment caused by diabetes is intended, step S104 and thereafter are not necessarily required.

When reproduction of the patient experience content data 103c is finished through the operation of the content reproducer formed by execution of the content reproduction program 103a, the virtual reality video reproduction apparatus 100 reads the video data of the lifestyle habit description content data 103d, generates the virtual reality video and causes the electronic display 104 to display the video (step S104). That is, the virtual reality video reproduction apparatus 100 sequentially reads, from the memory 103, a series of images of the 360-degree video of the lifestyle habit description video of the lifestyle habit description content data 103d. If the images are encoded video data, this apparatus decodes the data, takes data on the images constituting the video, and deploys the data on the RAM 102. The virtual reality video reproduction apparatus 100 takes, from the data on decoded images, an area of the images to be viewed in the direction toward the front of the virtual reality video reproduction apparatus 100 detected by the sensor 105 (direction of the user's line of sight), and performs deformation (coordinate transformation) based on appropriate perspective, thereby generating the images constituting the virtual reality video that provides the user with a view as if the user viewing the video felt on site in a three-dimensional space. The data on the images are transferred to the data buffer area of the electronic display 104, and is displayed.

Figure 14:
FIG. 14 shows an example of a screen of content representing "advice for lifestyle habit improvement".

The virtual reality video reproduction apparatus 100 always monitors whether the reproduction of video data on the lifestyle habit description content data 103d is finished or not through the operation of the content reproducer formed by execution of the content reproduction program 103a. If not finished, the processing in the flow is returned to step S104, and the virtual reality video of the lifestyle habit description content data 103d is continuously displayed. If finished, displaying of the virtual reality video is finished (step S105). Data identifying the time of finish of the lifestyle habit description content data 103d may be included in the lifestyle habit description content data 103d, or held as other data different therefrom. FIG. 14 shows an example of a screen of content that represents a situation where advice is taken from the family as advice for lifestyle habit improvement.

The user views the content of the patient experience video that simulates the visual impairment through reproduction of the patient experience content data 103c, experiences the symptom of the complication of diabetes with a sense of immersion, and subsequently views the content of the lifestyle habit description video through reproduction of the lifestyle habit description content data 103d. Accordingly, the user is strongly motivated to take advice for improving a lifestyle habit for the sake of preventing diabetes, preventing development, treatment and the like provided through the lifestyle habit description video of the lifestyle habit description content data 103d. Accordingly, the method of allowing the user to view the content of the patient experience content data 103c and the lifestyle habit description content data 103d provided by the virtual reality video reproduction apparatus 100 can function not only as awareness building for lifestyle habit improvement but also as a diabetes preventing method and a treatment method.

Configuration of Second Embodiment (Virtual Reality Video Reproduction Apparatus Based On Forward Video Pictures)

Figure 4:
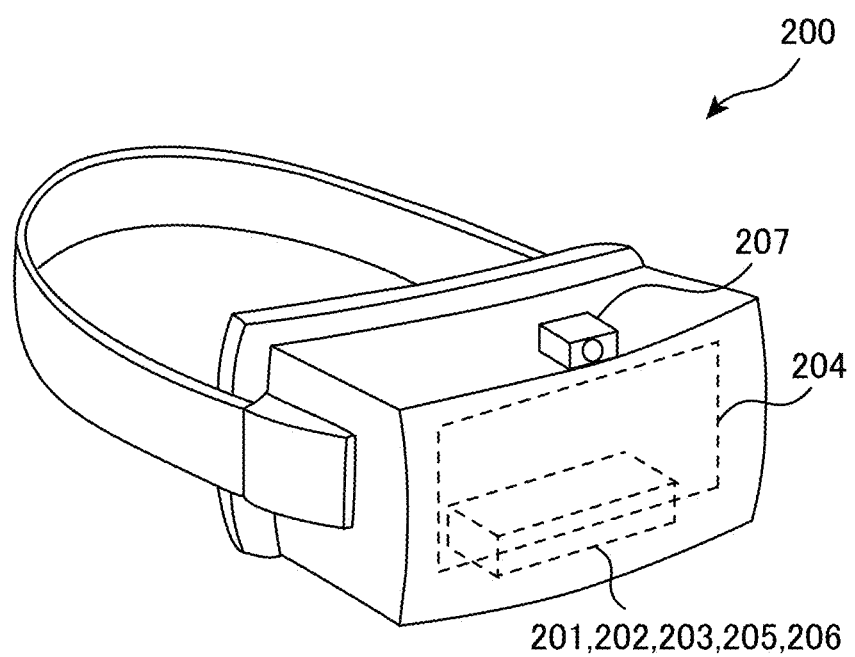
FIG. 4 shows a schematic appearance of the virtual reality video reproduction apparatus 200 according to the second embodiment of the present invention.

Next, a virtual reality video reproduction apparatus 200 according to the second embodiment of the present invention is described. The virtual reality video reproduction apparatus 200 according to the second embodiment includes some components similar to those of the virtual reality video reproduction apparatus 100 according to the first embodiment. Such similar components are represented by reference symbols with hundreds place digits of "1" being replaced with "2". Description of components of the virtual reality video reproduction apparatus 200 that have identical components, functions and the like of the virtual reality video reproduction apparatus 100 is appropriately omitted. FIG. 4 shows a schematic appearance of the virtual reality video reproduction apparatus 200. The virtual reality video reproduction apparatus 200 is an apparatus that allows the user to view the augmented reality video simulating a state of occurrence of the visual impairment in the user's visual field in real time, and subsequently allows the user to view the content of description of a lifestyle habit for preventing diabetes, preventing development thereof, or treatment therefor. Typically, the virtual reality video reproduction apparatus 200 is a mode of a virtual reality headset that is a head mount display (goggle) provided with an electronic display that displays a video representing a three-dimensional virtual reality.

Figure 2:
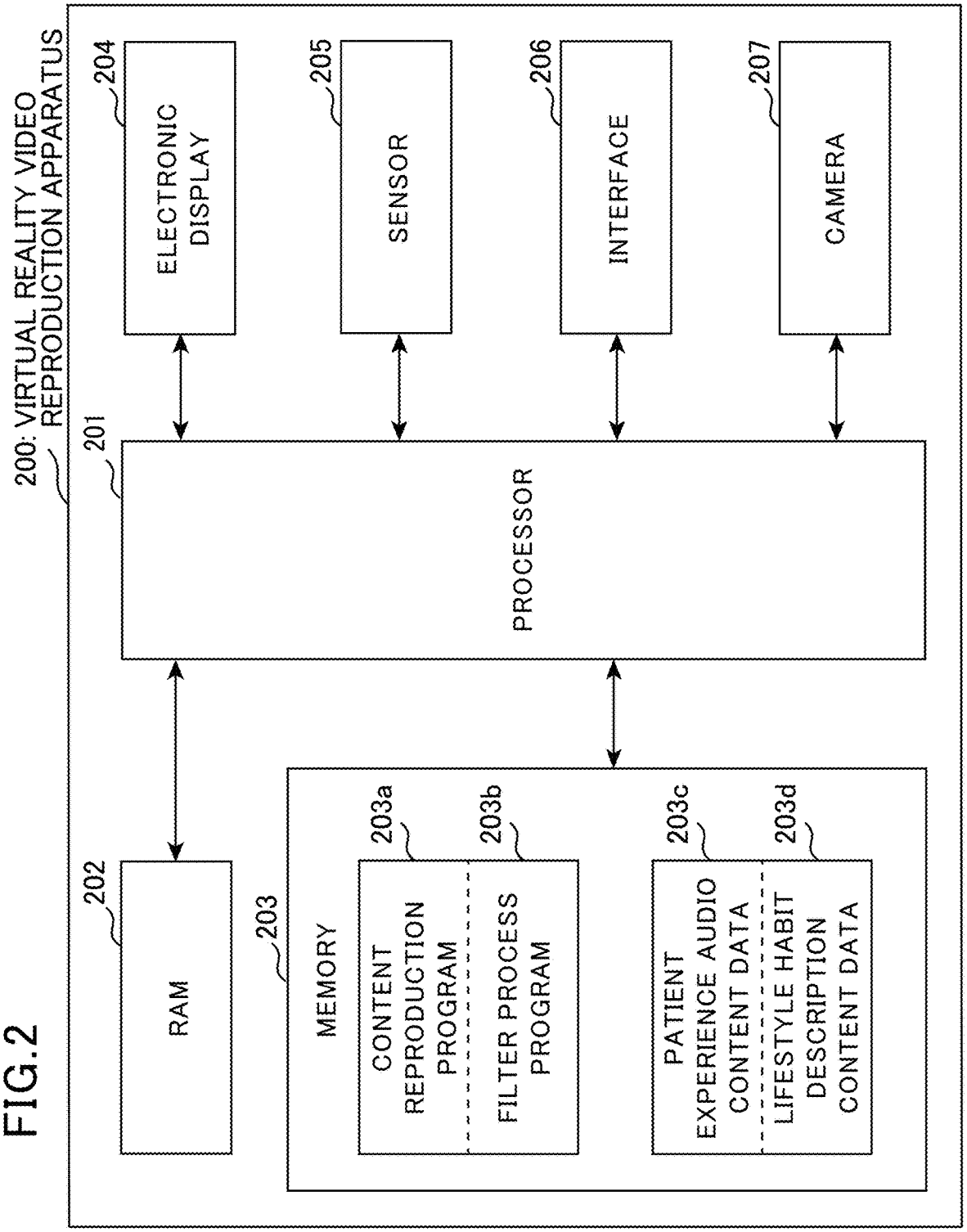
FIG. 2 is a block diagram showing the configuration of a virtual reality video reproduction apparatus 200 according to a second embodiment of the present invention.

FIG. 2 is a block diagram showing the configuration of the virtual reality video reproduction apparatus 200. The virtual reality video reproduction apparatus 200 includes a processor 201, a RAM 202, a memory 203, an electronic display 204, a sensor 205, an interface 206, and a camera 207. The processor 201, the RAM 202, the memory 203, the electronic display 204, the sensor 205 and the interface 206 have functions similar to those of the processor 101, the RAM 102, the memory 103, the electronic display 104, the sensor 105 and the interface 106. In the virtual reality video reproduction apparatus 200, content data stored in the memory 203 and the camera 207 are different from those in the virtual reality video reproduction apparatus 100. Accordingly, these components are described below.

The memory 203 stores, as content data, patient experience audio content data 203c and lifestyle habit description content data 203d. The patient experience audio content data 203c is content data on patient experience audio describing the visual impairment caused by diabetes on the basis of forward video pictures where a simulation of visual impairment is executed. The lifestyle habit description content data 203d is content data on a lifestyle habit description video that includes a description for a lifestyle habit to prevent diabetes and its worsening. As described above, the lifestyle habit description content data 203d is content data of a lifestyle habit description video similar to the lifestyle habit description content data 103d in the first embodiment. However, the patient experience audio content data 203c is different from the patient experience content data 103c in the first embodiment, and is audio content data instead of a video. The patient experience audio content data 203c is content data on patient experience audio that is obtained by simulating a symptom of visual impairment due to diabetes and overlaying the symptom on the forward video pictures representing the user's front scene, thereby guiding, through audio, development of a scenario for providing experience in real time through augmented reality. Here, the patient experience audio content data 203c is data characterized by including at least audio information that provides guidance of development of the scenario such that the user can be provided with a sense as if the user were experiencing the symptom of visual impairment when the simulation of the visual impairment caused by diabetes is performed for the forward video pictures to allow the user to view the video. The patient experience audio content data 203c may further include audio information for providing guidance for a behavior to provide an actual sense of visual impairment. When the patient experience audio content data 203c is reproduced, the patient experience audio is reproduced and output from a speaker, the forward video pictures representing the front scene to be in the user's visual field at a place where the user currently resides (unlike the first embodiment, the taken content-based patient experience video is not reproduced) is obtained through the camera 207. The filter process of simulating the visual impairment is applied to the forward video pictures. The user is allowed to view the filter-processed image, thereby overlaying the visual impairment in the user's actual visual field in real time to provide the user with experience as augmented reality. That is, the filter process in the second embodiment is applied to the forward video pictures instead of the patient experience video as the virtual reality video in the first embodiment. Note that the forward video pictures represent the actual visual range of the user wearing the virtual reality video reproduction apparatus 200. Accordingly, in terms of the three-dimensional video pictures (video) providing a sense as if the user were on site, the forward video pictures are conceivable as a type of a virtual reality video. The patient experience audio content data 203c does not necessarily require preliminarily taken video content. Specifically, the content of the patient experience audio of the patient experience audio content data 203c is data on guidance audio that includes a description of the visual impairment caused by diabetes, guidance of development of the scenario of starting the simulation of visual impairment for the own visual field represented by the forward video pictures, and guidance of a behavior providing an actual sense of the visual impairment such as looking around while the visual impairment is simulated on the forward video pictures, during their reproduction. Similar to the patient experience content data 103c, virtual reality content taken in accordance with a scenario can be combined and reproduced. The patient experience audio content data 203c may include scenario data for controlling the operation of the virtual reality video reproduction apparatus 200 for activating and stopping a predetermined process, such as a filter process at predetermined timing, when the content data is reproduced. Accordingly, in accordance with the scenario of the content, at timing when guidance of starting the simulation in the own visual field is provided through audio, the image processing of simulation of visual impairment can be started for the forward video pictures, and the effect is gradually increased to a predetermined intensity, and at timing when the effect becomes the predetermined intensity, guidance for looking around can be provided through audio.

The camera 207 is configured by combining a lens with an imaging element, such as a CMOS image sensor, and has a configuration of sequentially outputting data representing the images of the front scene image-formed on the imaging element every scanning time period, thereby outputting data representing the forward video pictures (front scene video). The camera 207 is attached to an upper part of an frontmost part of the virtual reality video reproduction apparatus 200 to be oriented forward so as to capture the forward scene of the imaging object in the angle of view. The data on the forward video pictures is temporarily deployed on the RAM 202.

Operation of Second Embodiment (Virtual Reality Video Reproduction Apparatus Based On Forward Video Pictures)

Figure 6:
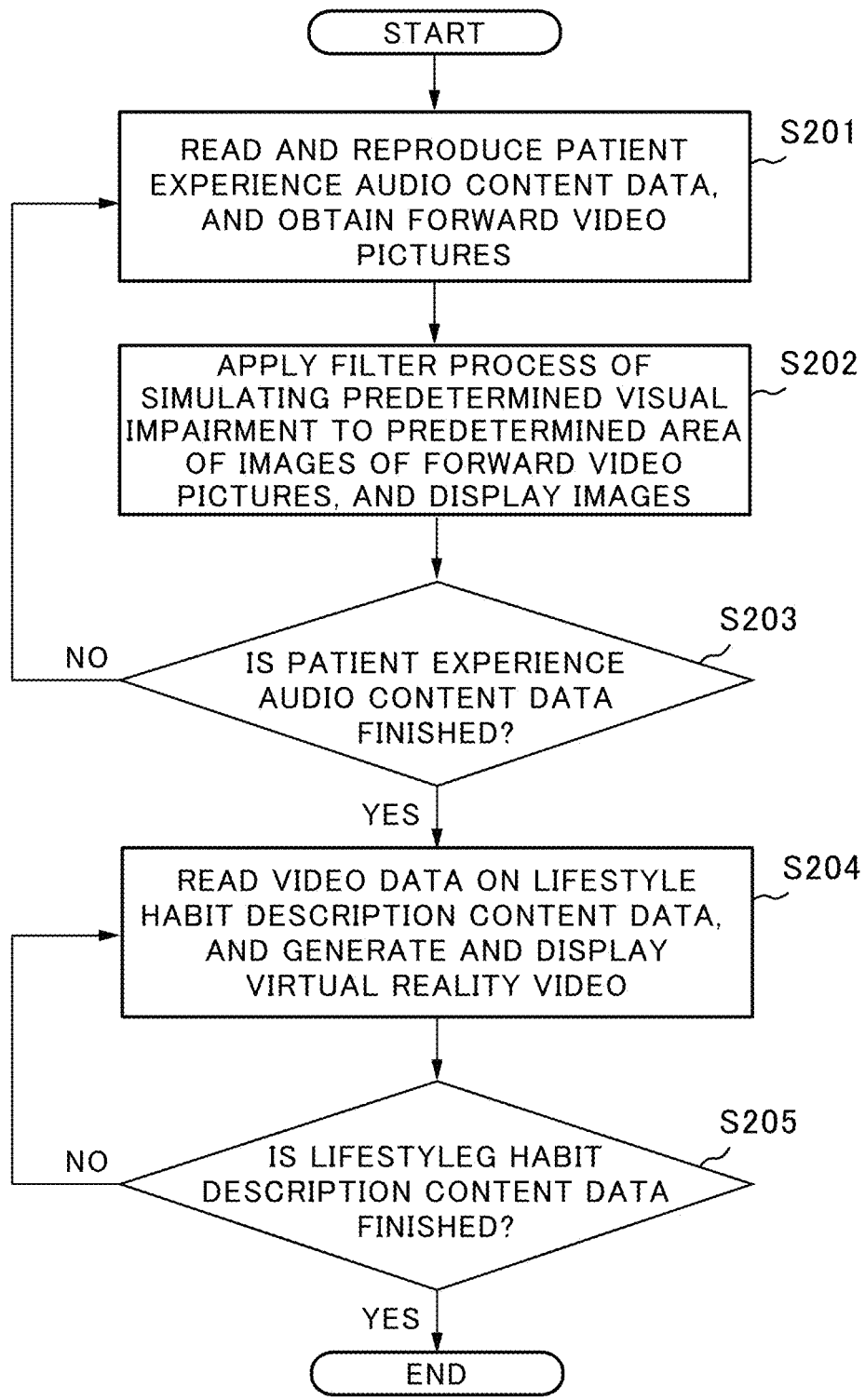
FIG. 6 is an operation flow diagram of the virtual reality video reproduction apparatus 200 according to the second embodiment of the present invention.

Next, the operation of the virtual reality video reproduction apparatus 200 is described. FIG. 6 is an operation flow diagram of the virtual reality video reproduction apparatus 200 according to the second embodiment. The virtual reality video reproduction apparatus 200 according to the second embodiment has operations similar or corresponding to those of the virtual reality video reproduction apparatus 100 according to the first embodiment. Such similar or corresponding operations are represented by reference symbols with hundreds place digits of "1" being replaced with "2". Description of the same operations of the virtual reality video reproduction apparatus 200 as the corresponding operations of the virtual reality video reproduction apparatus 100 is appropriately omitted.

When an instruction for content reproduction is input into the virtual reality video reproduction apparatus 200, the virtual reality video reproduction apparatus 200 first reads audio data on the patient experience audio content data 203*c* from the memory 203 through a content reproducer formed by execution of a content reproduction program 203*a*, reproduces guidance audio represented by the data, outputs the audio from the speaker or the like, and obtains video picture data (video data) on the forward video pictures representing the front scene obtained by the camera 207 (step S201). When the image of video picture data is displayed on the electronic display 204 with a correct scale, the natural image is provided to allow the user viewing the image to feel a sense of perspective as if the user were on site. The obtained video picture data is temporarily deployed on the RAM 202.

Next, the virtual reality video reproduction apparatus 200 applies the filter process to the obtained forward video picture data through the operation of the filter processor formed by execution of the filter process program 203*b*, and causes the electronic display 204 to display the video (step S202). That is, the virtual reality video reproduction apparatus 200 applies the filter process of simulating the visual impairment of "loss", "blearedness", "blurredness", "distortion" or the like to each of the images constituting the forward video pictures obtained and deployed on the RAM 202 in step S201, thereby generating the forward video pictures where the symptom of the visual impairment is overlaid, and transferring the pictures to the data buffer area of the electronic display 204 to be displayed. The type of the filter process, and the process for executing the process are the same as those described with respect to the virtual reality video reproduction apparatus 100. Accordingly, the visual impairment is simulated in the actual visual field of the user themself. Consequently, the viewing user is allowed to experience the visual impairment through augmented reality. Likewise with the description of the virtual reality video reproduction apparatus 100, the simulation of visual impairment may be started in the predetermined period during displaying, and the process of enhancing the effect may be performed. Likewise with the description of the virtual reality video reproduction apparatus 100, the multiple types of visual impairments may be sequentially simulated, and the visual impairments where the multiple types of visual impairments are overlaid may be simulated.

The virtual reality video reproduction apparatus 200 always monitors whether the reproduction of the audio data on the patient experience audio content data 203*c* is finished or not through the operation of the content reproducer formed by execution of the content reproduction program 203*a*. If not finished, the processing in the flow is returned to step S201, and the reproduction of the guidance audio of the patient experience audio content data 203*c*, and displaying of the filter-processed forward video pictures are continued. If finished, the processing in the flow proceeds to the next step S204 (step S203). The user views the forward video pictures where the visual impairment is simulated through reproduction of the patient experience audio content data 203*c* in their visual field with guidance audio thereof, and can experience the symptom of visual impairment caused by diabetes with a sense of immersion. Note that step S204 and thereafter indicate reproduction of the lifestyle habit description content data 203*d*. If only experience of the symptom of the visual impairment caused by diabetes is intended, step S204 and thereafter are not necessarily required.

When reproduction of the audio data of the patient experience audio content data 203*c* is finished through the operation of the content reproducer formed by execution of the content reproduction program 203*a*, the virtual reality video reproduction apparatus 200 reads the video data on the lifestyle habit description content data 203*d*, generates the virtual reality video and causes the electronic display 204 to display the video (step S204). The virtual reality video reproduction apparatus 200 always monitors whether the reproduction of video data on the lifestyle habit description content data 203*d* is finished or not through the operation of the content reproducer formed by execution of the content reproduction program 203*a*. If not finished, the processing in the flow is returned to step S204, and virtual reality video of the lifestyle habit description content data 203*d* is continuously displayed. If finished, displaying of the virtual reality video is finished (step S205). The user views the forward video pictures where the visual impairment is simulated by reproduction of the patient experience audio content data 203*c* and the filter processing for the forward video pictures, experiences the symptom of the visual impairment caused by diabetes as their own symptom in real time through augmented reality with a sense of immersion, and subsequently views the lifestyle habit description video through reproduction of the lifestyle habit description content data 203*d* through virtual reality with a sense of immersion. Accordingly, the user is strongly motivated to take advice for improving a lifestyle habit for the sake of preventing diabetes, preventing development, treatment and the like provided through the lifestyle habit description video of the lifestyle habit description content data 203*d*. As described above, the method of allowing the user to view the content provided by the virtual reality video reproduction apparatus 200 can function not only as awareness building for lifestyle habit improvement but also as a diabetes preventing method and a treatment method.

Characteristics of Simulation of Visual Impairment Common to First and Second Embodiments The first embodiment and the second embodiment have thus been described above. These embodiments are different from each other in that the three-dimensional video where the simulation of visual impairment is executed is the virtual reality video that represents the virtual reality content preliminarily imaged in the first embodiment, and the forward video pictures through augmented reality representing the front scene to be in the visual field of the user in the second embodiment. However, these embodiments are common in that the embodiments have the configuration where the simulation of visual impairment is executed for the three-dimensional video providing the user with a sense as if they were on site, and the execution is overlaid on the original video.

The present invention is not limited to the specific embodiments described above. The configuration elements or information processing in the disclosed embodiments can be combined, deformed or omitted in a range of the technical thought of the present invention, and can be executed.

INDUSTRIAL APPLICABILITY

The apparatus of the present invention allows the user to experience the visual impairment caused by diabetes through virtual reality or augmented reality, thereby strongly impressing potential patients with the seriousness of diabetes with a sense of immersion. Accordingly, in the field of the virtual reality technology or augmented reality technology, medicine or preventive medicine, in order to prevent diabetes, the apparatus can be widely used for allowing the potential patients to be aware of diabetes. In the case where the user experiences the visual impairment caused by diabetes through virtual reality or augmented reality and subsequently views the content of advice for lifestyle habit improvement through virtual reality, the method of using the apparatus of the present invention can be used as the diabetes preventing method or treatment method in the fields of medicine and preventive medicine.

REFERENCE SIGNS LIST

100: Virtual reality video reproduction apparatus
101: Processor
102: RAM
103: Memory
103a: Content reproduction program
103b: Filter process program
103c: Patient experience content data
103d: Lifestyle habit description content data
104: Electronic display
105: Sensor
106: Interface
200: Virtual reality video reproduction apparatus
201: Processor
202: RAM
203: Memory
203a: Content reproduction program
203b: Filter process program
203c: Patient experience audio content data
203d: Lifestyle habit description content data
204: Electronic display
205: Sensor
206: Interface
207: Camera

The invention claimed is:

1. A virtual reality video reproduction apparatus, comprising:
  a memory that stores content data including virtual reality content,
  a virtual reality headset that includes a camera that obtains forward video pictures, and an electronic display for displaying the forward video pictures and a virtual reality video about the virtual reality content,
  a content reproducer that generates the virtual reality video that represents the virtual reality content, from the content data, and
  a filter processor that executes a filter process of applying a predetermined image processing to a predetermined area of at least part of images of the forward video pictures, and causes the electronic display to display the forward video pictures,
  wherein the filter process executes, as the predetermined image processing, a simulation of a visual impairment caused by diabetes,
  wherein the content data includes patient experience audio content describing, by audio, the visual impairment caused by diabetes based on the forward video pictures where the simulation of the visual impairment is executed, and
  wherein the content reproducer further reproduces the audio from the patient experience audio content, before reproduction of the virtual reality content.

2. The virtual reality video reproduction apparatus according to claim 1, wherein the virtual reality content includes lifestyle habit description content taken in accordance with a scenario describing a lifestyle habit for preventing diabetes, preventing development thereof, or treatment therefor, after the patient experience audio content.

3. The virtual reality video reproduction apparatus according to claim 1, wherein the filter process executes the simulation in which an effect of the simulation is enhanced to a predetermined intensity such that the visual impairment starts and gradually develops to a predetermined degree.

4. The virtual reality video reproduction apparatus according to claim 1, wherein the filter process executes the simulation of the visual impairment of loss, by darkening the predetermined area of the at least part of the images.

5. The virtual reality video reproduction apparatus according to claim 1, wherein the filter process executes the simulation of the visual impairment of blearedness, by blearing the predetermined area of the at least part of the images.

6. The virtual reality video reproduction apparatus according to claim 1, wherein the filter process executes the simulation of the visual impairment of blurredness, by blurring the predetermined area of the at least part of the images.

7. The virtual reality video reproduction apparatus according to claim 1, wherein the filter process executes the simulation of the visual impairment of distortion, by distorting the predetermined area of the at least part of the images.

8. A method of using a virtual reality video reproduction apparatus, for preventing diabetes, preventing development thereof, or treatment therefor, the virtual reality video reproduction apparatus comprising:
  a virtual reality headset that includes a camera that obtains forward video pictures, and an electronic display for displaying the forward video pictures and a video about virtual reality content; and
  a filter processor that executes a filter process of executing a simulation of a visual impairment caused by diabetes for a predetermined area of at least part of images of the forward video pictures, and causes the electronic display to display the forward video pictures,
wherein the method comprises a step of:
  applying the filter process to the forward video pictures and causing the electronic display to display the forward video pictures, while reproducing patient experience audio content that describes the visual impairment caused by diabetes, based on the forward video pictures where the simulation of the visual impairment is executed.

9. The method according to claim 8, further comprising: reproducing lifestyle habit description content that is the virtual reality content taken in accordance with a scenario describing a lifestyle habit for preventing diabetes, preventing development thereof, or treatment therefor, after reproducing the patient experience audio content, and causing the electronic display to display the lifestyle habit description content.

10. The method according to claim 8, wherein the filter process executes the simulation in which an effect of the simulation is enhanced to a predetermined intensity such that the visual impairment starts and gradually develops to a predetermined degree.

11. The method according to claim 8, wherein the filter process executes the simulation of the visual impairment of loss, by darkening the predetermined area of the at least part of the images.

12. The method according to claim 8, wherein the filter process executes the simulation of the visual impairment of blearedness, by blearing the predetermined area of the at least part of the images.

13. The method according to claim 8, wherein the filter process executes the simulation of the visual impairment of blurredness, by blurring the predetermined area of the at least part of the images.

14. The method according to claim 8, wherein the filter process executes the simulation of the visual impairment of distortion, by distorting the predetermined area of the at least part of the images.

\* \* \* \* \*